(12) United States Patent
Umezawa et al.

(10) Patent No.: US 9,360,551 B2
(45) Date of Patent: Jun. 7, 2016

(54) OBJECT INFORMATION ACQUIRING APPARATUS AND CONTROL METHOD THEREOF

(71) Applicant: CANON KABUSHIKI KAISHA, Tokyo (JP)

(72) Inventors: Kohtaro Umezawa, Kyoto (JP); Takuji Oishi, Kyoto (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 440 days.

(21) Appl. No.: 13/900,891

(22) Filed: May 23, 2013

(65) Prior Publication Data

US 2013/0336088 A1 Dec. 19, 2013

(30) Foreign Application Priority Data

Jun. 13, 2012 (JP) ................................. 2012-133801

(51) Int. Cl.
*G01S 15/00* (2006.01)
*G01S 15/89* (2006.01)
*A61B 5/00* (2006.01)

(52) U.S. Cl.
CPC ............... *G01S 15/89* (2013.01); *A61B 5/0095* (2013.01)

(58) Field of Classification Search
CPC .............................. G01S 15/89; A61B 5/0095
See application file for complete search history.

(56) References Cited

U.S. PATENT DOCUMENTS

| 2008/0226149 | A1* | 9/2008 | Wischmann et al. | 382/131 |
|---|---|---|---|---|
| 2009/0297006 | A1* | 12/2009 | Suri et al. | 382/131 |
| 2010/0191117 | A1* | 7/2010 | Kabakov | 600/453 |
| 2011/0125017 | A1* | 5/2011 | Ramamurthy et al. | 600/443 |
| 2011/0201933 | A1* | 8/2011 | Specht et al. | 600/443 |
| 2011/0245652 | A1 | 10/2011 | Oishi | 600/407 |
| 2011/0251505 | A1* | 10/2011 | Narayan et al. | 600/515 |
| 2012/0016209 | A1* | 1/2012 | Wolfberg et al. | 600/301 |
| 2012/0183190 | A1 | 7/2012 | Fukutani et al. | 382/128 |
| 2012/0289812 | A1 | 11/2012 | Oishi | 600/407 |
| 2013/0160558 | A1 | 6/2013 | Oishi | 73/655 |
| 2013/0261427 | A1 | 10/2013 | Oishi | 600/407 |

OTHER PUBLICATIONS

S. Wang et al., "Noninvasive Imaging of Hemoglobin Concentration and Oxygenation in the Rat Brain Using High-Resolution Photoacoustic Tomography", *Journal of Biomedical Optics* 11(2), 024015-1 through 024015-9 (Mar./Apr. 2006).

* cited by examiner

*Primary Examiner* — Luke Ratcliffe
*Assistant Examiner* — Hovhannes Baghdasaryan
(74) *Attorney, Agent, or Firm* — Fitzpatrick, Cella, Harper & Scinto

(57) ABSTRACT

Provided is an object information acquiring apparatus that generates image data inside an object on the basis of an acoustic wave propagating inside the object, which uses an object information acquiring apparatus having an acoustic detector receiving the acoustic wave, an object information distribution processor generating an object information distribution representing a property of inside of the object by using the acoustic wave, a reliability distribution generator generating a reliability distribution by using the object information distribution, a similarity distribution generator generating a similarity distribution indicating similarity between template data indicating a relation between a real image and an artifact in the image data, and the object information distribution, and a combination processor performing combination processing of the reliability distribution and the similarity distribution.

22 Claims, 14 Drawing Sheets

OBJECT INFORMATION ACQUIRING APPARATUS AND CONTROL METHOD THEREOF

BACKGROUND OF THE INVENTION

1. Field of the Invention

The present invention relates to an object information acquiring apparatus and a control method thereof.

2. Description of the Related Art

Object information acquiring apparatuses using X-rays and ultrasound waves have been used in many fields requiring non-destructive inspection, mainly the medical field. In the medical field, physiological information (i.e., functional information) about a biological body is effective for discovery of a disease such as cancer. Therefore, study of imaging of the functional information has recently been conducted. As one example of diagnostic methods using the functional information, photoacoustic tomography (PAT), an optical imaging technique, is proposed. While only morphometric information in a biological body is obtained in an X-ray diagnosis or an ultrasound wave diagnosis, both morphometric information and functional information can be non-invasively obtained in photoacoustic tomography.

In photoacoustic tomography, pulsed light generated from a light source is first emitted into an object. Then, an acoustic wave (typically, an ultrasound wave) is generated from an inner tissue of the object absorbing light propagated and diffused in the object by the photoacoustic effect. This acoustic wave is detected by a probe or the like, whereby the imaging of the information of the inner tissue that is a generation source of the acoustic wave is enabled. Change of the received acoustic wave over time is detected at a plurality of portions surrounding the object, and analytical processing (reconstruction) is mathematically performed for an obtained signal, whereby information associated with an optical characteristic value inside the object can be three-dimensionally visualized. This information can be used as morphometric information inside the object. Furthermore, the functional information including an optical characteristic value distribution such as an absorption coefficient distribution inside the object can be obtained from an initial sound pressure generation distribution generated by emitting light into the object.

For example, near-infrared light can be used as pulsed light emitted into the object. The near-infrared light has a property of being likely to transmit through water that constitutes most of a biological body, and to be absorbed in hemoglobin in blood, and therefore imaging of a blood vessel image using morphometric information is enabled. Furthermore, it is possible to know the content rate of oxygenated hemoglobin to total hemoglobin in the blood, namely, an oxygen saturation by using the absorption coefficient distribution obtained by emitting near-infrared light, and also possible to perform imaging of a biological body function. An oxygen saturation distribution serves as an index distinguishing between benignity and malignity of a tumor, and is therefore expected as an effective means of discovery of a malignant tumor.

The calculation of the oxygen saturation is performed by a comparison operation in which measurement is performed a plurality of times with pulsed light having different wavelengths, and a ratio of absorption coefficients calculated respectively is calculated. This uses a principle that since the optical absorption spectra of deoxygenated hemoglobin and oxygenated hemoglobin are different, the respective content rates are found by performing measurement at different wavelength and comparing the spectra.

In a case of the aforementioned imaging, when the comparison operation calculating the ratios is performed with no change, a blood vessel image portion and a background portion cannot be distinguished. Therefore, as described in Xueding Wang, et al. "Noninvasive imaging of hemoglobin concentration and oxygenation in the rat brain using high-resolution photoacoustic tomography", *Journal of Biomedical Optics* 11(2), 024015 (March/April 2006), the blood vessel image portion and the background portion need to be distinguished and only the blood vessel image portion needs to be processed.

Non Patent Literature 1: Xueding Wang, et al. "Noninvasive imaging of hemoglobin concentration and oxygenation in the rat brain using high-resolution photoacoustic tomography" *Journal of Biomedical Optics* 11(2), 024015 (March/April 2006)

SUMMARY OF THE INVENTION

Heretofore, in order to distinguish between a real image portion such as a blood vessel image and a background portion, a threshold value method is employed. In this method, a threshold value of an optical characteristic value (e.g., absorption coefficient) is set. Then, for each voxel, a case of having a voxel value not smaller than the threshold value is determined as the real image portion, and a case of having a voxel value smaller than the threshold value is determined as the background portion. However, this threshold value method encounters a problem in that the real image portion and the background portion can not successfully distinguished in a case where the contrast of both is weak.

Examples of a case where the contrast of an optical characteristic value distribution is weak include a case where a noise of the background portion is large and therefore a voxel value of the background portion is equivalent to that of the real image portion, and a case where the voxel value of the background portion is larger. In such cases, in the threshold value method, the background portion and the real image portion cannot be distinguished. This is a problem not only for the threshold value method, but for all methods of distinguishing between the background portion and the real image portion by utilizing voxel values. Particularly, the contrast is deteriorated on a deep portion of a biological body, and therefore it is difficult to distinguish between the real image portion and the background portion on the deep portion of the biological body.

The present invention has been conceived in order to solve the aforementioned problems, and an object thereof is to provide a technique for successfully distinguishing between a real image and an artifact, and a background in an object information acquiring apparatus using acoustic waves.

The present invention provides an object information acquiring apparatus generating image data inside an object on the basis of an acoustic wave propagating inside the object, the object information acquiring apparatus comprising:

an acoustic detector configured to receive the acoustic wave;

an object information distribution processor configured to generate an object information distribution representing a property of inside of the object by using the acoustic wave;

a reliability distribution generator configured to generate a reliability distribution by using the object information distribution;

a similarity distribution generator configured to generate a similarity distribution between template data indicating a relation between a real image and an artifact in the image data, and the object information distribution; and a combination processor configured to perform combination processing of the reliability distribution and the similarity distribution.

The present invention also provides a control method of an object information acquiring apparatus generating image data inside an object on the basis of an acoustic wave propagating inside the object, the control method comprising the steps of:
receiving the acoustic wave;
generating an object information distribution representing a property of inside of the object by using the acoustic wave;
generating a reliability distribution by using the object information distribution;
generating a similarity distribution between template data indicating a relation between a real image and an artifact in the image data, and the object information distribution; and
performing combination processing of the reliability distribution and the similarity distribution.

According to the present invention, it is possible to provide a technique for successfully distinguishing between a real image and an artifact, and a background in an object information acquiring apparatus using acoustic waves.

Further features of the present invention will become apparent from the following description of exemplary embodiments with reference to the attached drawings.

DESCRIPTION OF THE EMBODIMENTS

Figure 1:
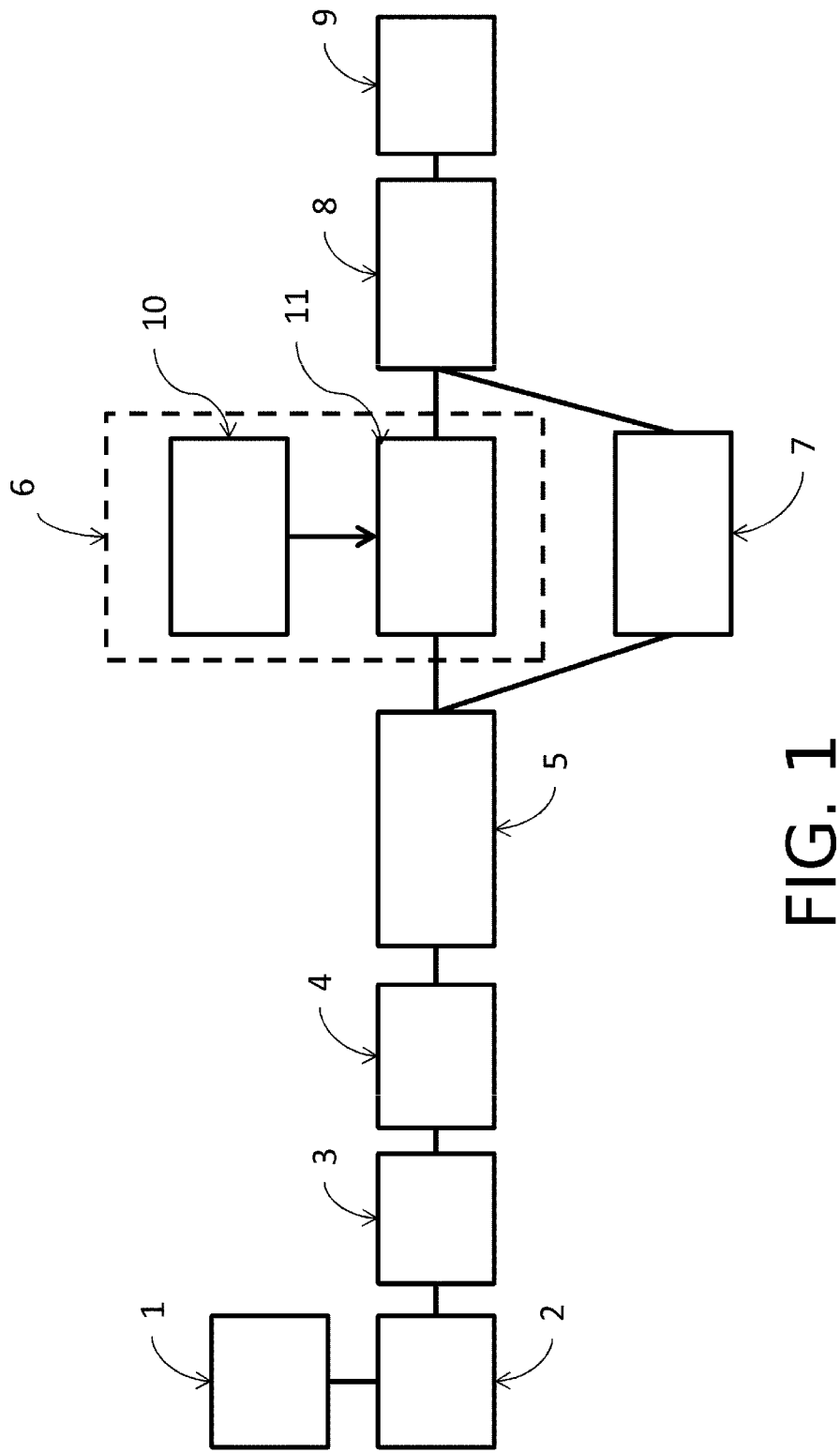
FIG. 1 is a schematic diagram showing a configuration of a device according to a first embodiment.

Hereinafter, preferred embodiments of the present invention will be described with reference to the drawings. However, size, quality of materials, shape of components, relative arrangement thereof, and the like should be appropriately changed according to a configuration of an apparatus to which the invention is applied, or various conditions, and the scope of this invention is not limited to the description described below.

An object information acquiring apparatus of the present invention receives an acoustic wave generated or reflected, and propagated inside an object by using an acoustic wave detector. The object information acquiring apparatus of the present invention includes a device which utilizes an ultrasound wave echo technique of transmitting an ultrasound wave to the object, receiving a reflected wave (reflected ultrasound wave) reflected on the inside of the object, and acquiring an object information distribution as image data. The object information acquiring apparatus further includes a device which utilizes a photoacoustic effect of receiving an acoustic wave (typically, an ultrasound wave) generated inside the object by emitting light (electromagnetic wave) to the object, and acquiring the object information distribution as image data.

In a case of the former device utilizing the ultrasound wave echo technique, the object information is information reflecting difference in acoustic impedance of tissues inside the object. In a case of the latter apparatus utilizing the photoacoustic effect, the object information indicates a generation source distribution of acoustic waves generated by light application, or an initial sound pressure distribution inside the object, an optical energy absorption density distribution or an absorption coefficient distribution derived from the initial sound pressure distribution, or a concentration information distribution of substances configuring tissues. Examples of the concentration information distribution of substances include an oxygen saturation distribution, an oxygenated/reduced hemoglobin concentration distribution, and the like, for example.

An acoustic wave in the present invention is typically an ultrasound wave, and includes an elastic wave referred to as a sound wave, an ultrasound wave, or an acoustic wave. For example, examples of the acoustic wave include an acoustic wave generated inside the object when light such as near-infrared light is emitted into the object. An acoustic wave generated by a photoacoustic effect is referred to as a photoacoustic wave, or a light-induced ultrasound wave. An acoustic detector (e.g., a probe) receives acoustic waves generated or reflected inside the object.

In the following embodiment, a photoacoustic device which forms at least one kind of the object information distribution by a photoacoustic tomography technique will be mainly described. However, the present invention is not limited to this. The technique of the present invention is applicable to various object information acquiring apparatuses.

Additionally, the range of application of the present invention is not limited to only a single device. For example, the present invention can be achieved as a method of distinguishing between a real image and an artifact, or a program for implementing this distinguishing method.

The present invention utilizes a constant relation between the real image and the artifact (virtual image), and distinguishes between the real image and a background or the artifact by further adding reliability to the aforementioned relation. The real image indicates an image as which a light absorber with a large light absorption coefficient inside the object appears when performing imaging of the object information. The artifact is a virtual image corresponding to a real image, which appears by a response characteristic of the acoustic detector, or by processing during reconstruction (imaging). On the other hand, the background appears as a noise component of the object information.

First Embodiment

First, a basic embodiment of the present invention will be described.

<Configuration of Device>

As shown in FIG. 1, a device of the present embodiment is configured from a light source 1, a light irradiation device 2, an acoustic detector 4, an object information distribution processor 5, a similarity distribution generation device 6, a reliability distribution generator 7, a combination processor 8, and a display unit 9. The similarity distribution generation device 6 includes template data 10, and a matching processor 11. An object 3 is an object to be measured, and for example, a segment (e.g., breast) of an object to be tested, a biological body such as small animals, and an artificial object such as simulated biological bodies can be also measured.

(Light Source)

The light source 1 is a device generating pulsed light. Although a laser is desirable as the light source in order to obtain high output, a light-emitting diode or the like may be employed. In order to effectively generate photoacoustic waves, light must be emitted in enough short time in accordance with a heat characteristic of the object. In the present embodiment, it is assumed that the object is a biological body, and therefore it is desirable that a pulse width of pulsed light generated from the light source 1 is not more than several ten nanoseconds. A wavelength of the pulsed light is desirably in a near-infrared region of about 500 nm to 1200 nm, called a window of the biological body. Light of this region can reach a relatively deep portion of the biological body, and therefore information about the deep portion can be obtained. Furthermore, the wavelength of the pulsed light desirably has a high absorption coefficient with respect to an object to be observed.

(Light Irradiation Device)

The light irradiation device 2 is a device guiding the pulsed light generated by the light source 1 to the object 3. Specifically, examples of the light irradiation device include optical devices such as an optical fiber, a lens, a mirror, and a diffuser panel. Additionally, when guiding the pulsed light, shape or light density can be changed by using these optical devices. The optical devices are not limited to devices described herein, and any device may be employed as long as such a function is satisfied.

(Object)

As the object 3 serving as an object to be measured, a biological body or a phantom obtained by simulating an acoustic property and an optical property of the biological body can be used. The acoustic property is specifically propagation velocity and a decay rate of acoustic waves, and the optical property is specifically an absorption coefficient and a scattering coefficient of light.

Light absorbers having a large light absorption coefficient need to exist inside the object. Specifically, examples of the light absorbers include hemoglobin, water, melanin, collagen, and lipid in a case of the biological body. In a case of the phantom, substances obtained by simulating the optical properties of these are sealed inside the phantom as the light absorbers.

(Acoustic Detector)

The acoustic detector 4 is acoustically coupled to the object, receives a photoacoustic wave to convert the same to an electric signal (received signal), and amplifies the obtained analog electric signal to convert the same to a digital signal. In photoacoustic tomography, acoustic waves must be captured at a plurality of places, and therefore a 2D-type acoustic detector, in which a plurality of acoustic detection elements is arranged on a plane, is desirably used. However, the acoustic waves may be captured by using a 1D-type acoustic detector, in which acoustic detection elements are aligned, or a single acoustic detection element, and moving the same to a plurality of places by a scanning device.

As the acoustic detector, an acoustic detector having high sensitivity and a wide frequency band is desirably used, and specifically, examples thereof include acoustic detectors using PZT, PVDF, cMUT, and Fabry-Perot interferometry. However, the acoustic detector is not limited to the detectors described herein, and any detectors may be used as long as a function of capturing acoustic waves is satisfied. Additionally, as to conversion from an analog signal to a digital signal, although the number of the acoustic detectors is desirably the same as the number of analog-digital converters (ADC) in order to effectively acquire data, a single ADC may be connected to each of the acoustic detectors in sequence.

(Object Information Distribution Processor)

The object information distribution processor 5 performs processing of filtering digital signals obtained at respective positions and performing back projection from the respective positions. By this processing, an object information distribution (initial sound pressure distribution, etc.) indicating a position of a sound source is acquired as data for each unit area (pixel or voxel). Examples of the object information distribution processor specifically include a computer, an electric circuit, and the like.

(Similarity Distribution Generation Device)

As shown in FIG. 1, the similarity distribution generation device 6 is configured by the template data 10, and the matching processor 11. The template data 10 is readably held by a template data holder having an information storage function. The template data 10 is an object information distribution such as an initial sound pressure distribution serving as a template indicating the relation between a real image and an artifact behind the real image. The similarity distribution generation device corresponds to a similarity distribution generator of the present invention.

The matching processor 11 calculates similarity of the template data and the object information distribution such as the initial sound pressure distribution, and acquires a similarity distribution. In a case where the template data is not voxel data, voxel data for matching is calculated from the template data, and the similarity distribution of the calculated voxel data, and the object information distribution is acquired. Examples of the similarity distribution generation device specifically include a computer, an electric circuit, and the like.

(Reliability Distribution Generator)

The reliability distribution generator 7 generates a reliability distribution based on the object information distribution as image data by processing the image data obtained by the object information distribution processor 5. Examples of the reliability distribution generator specifically include a computer, an electric circuit, and the like.

(Combination Processor)

The combination processor 8 performs combination processing for image data obtained by the similarity distribution generation device 6 and image data obtained by the reliability distribution generator 7, and acquires a post-combination processing distribution as image data. Here, the combination is desirably a product of the image data obtained by the similarity distribution generation device 6, and the image data obtained by the reliability distribution generator 7, but may be a product with a reliability distribution normalized by a maximum value of the reliability distribution.

(Display Unit)

The display unit 9 displays image data generated by the combination processor 8 as an image. Examples of the display unit specifically include displays of a computer, television and the like.

<Flow of Processing>

Outline of the present invention is a procedure of obtaining a similarity distribution by the similarity distribution generation device 6 by utilizing data generated by the object information distribution processor 5, obtaining a reliability distribution by the reliability distribution generator 7, and performing combination processing by the combination processor 8. This procedure enables a real image derived from an absorber, and a background or an artifact to be distinguished, and enables an absorber region to be visually recognized from a displayed distribution.

Figure 3:
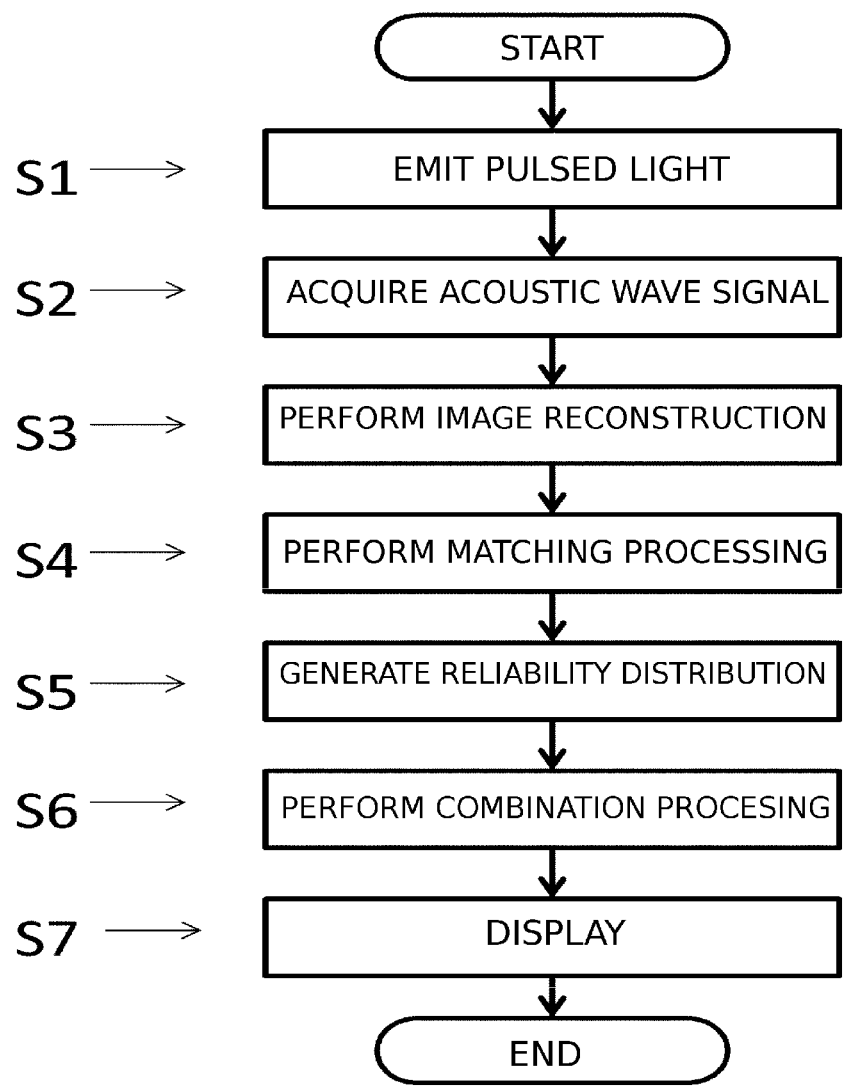
FIG. 3 is a flowchart showing an operation of the device according to the first embodiment.

Summary of the procedure based on such a principle will be described with reference to a flowchart of FIG. 3.

(Step S1) First, the light source 1 generates pulsed light, and the light irradiation device 2 emits pulsed light to the object 3.

(Step S2) The acoustic detector 4 detects an acoustic wave generated in the object 3.

(Step S3) The object information distribution processor 5 performs image reconstruction processing by using obtained signal.

(Step S4) The matching processor 11 of the similarity distribution generation device 6 performs matching processing by using the template data 10.

(Step S5) A reliability distribution is generated. In the present embodiment, an initial sound pressure distribution generated in S3 is used as the reliability distribution. Either Step S4 or Step S5 may be performed first.

(Step S6) Combination processing is performed. In the present embodiment, a product of values of the similarity distribution and the reliability distribution are taken as the combination processing.

(Step S7) Finally, a result of the combination is displayed on the display unit 9.

<Details of Processing>

The processing of each step will be described in detail. First, the relation between a real image, and an artifact and a background in an image generated by the object information distribution processor 5 will be described. Secondly, the processing in the reliability distribution generator 7 will be described. Then, the processing performed by using the template data 10 by the matching processor 11 in the similarity distribution generation device 6 will be described. Finally, the combination of the respective processing in the combination processor 8 will be described.

(Relation Between Real Image and Artifact in Image Reconstruction)

In Step S3, image reconstruction performed by the object information distribution processor 5 is performed by a method called back projection (or universal back projection). In this method, a concentric sphere centered on a position of a detector in three-dimensional space is drawn in proportion to a value obtained by differentiating a signal and inverting positive and negative. Then, voxel data is generated by superimposing results obtained by performing this processing for a plurality of detectors, and an initial sound source position is found out. However, an artifact (also referred to as a ghost) which does not exist in an original object may appear by overlapping in the back projection.

When the acoustic detectors are arranged so as to spherically surround the object, portions other than the original real image are completely cancelled by the superimposition in the back projection, and only the real image remains. Therefore, a problem due to the artifact hardly occurs.

However, when the arrangement of the detectors is planar, and only the acoustic waves at a part of angles can be received, the cancel becomes incomplete. Therefore, as shown in FIG. 2A, artifacts of negative values appear on the front and back of the real image as viewed from an acoustic detector side.

Furthermore, in a case where a frequency band of the acoustic detector is finite, a signal cannot be reproduced completely, and an obtained signal includes ringing. During back projection, this ringing becomes an artifact. This appears as an artifact on the further back (at a farther position as viewed from the acoustic detector) of the aforementioned artifact of the negative value as viewed from the acoustic detector side, as shown in FIG. 2B.

Figure 2A:
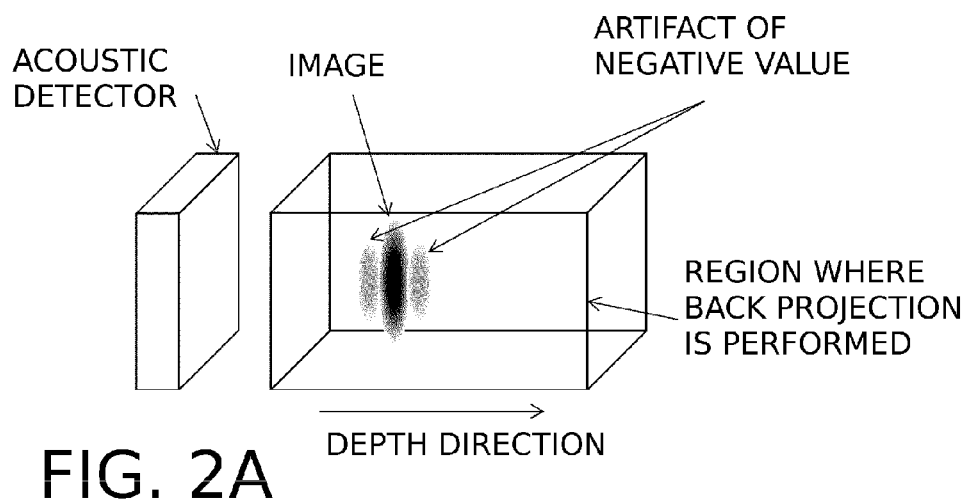
FIGS. 2A and 2B each are a figure showing the relation between a real image and an artifact.

In a situation as shown in FIG. 2A, the real image, and the artifacts of the negative value located on the front and back of the real image each result from the fall and the rise of a single signal, and therefore are always in contact with each other. An intensity ratio thereof is also constant for the same reason. Additionally, dimensional ratios of the both are substantially the same.

Figure 2B:
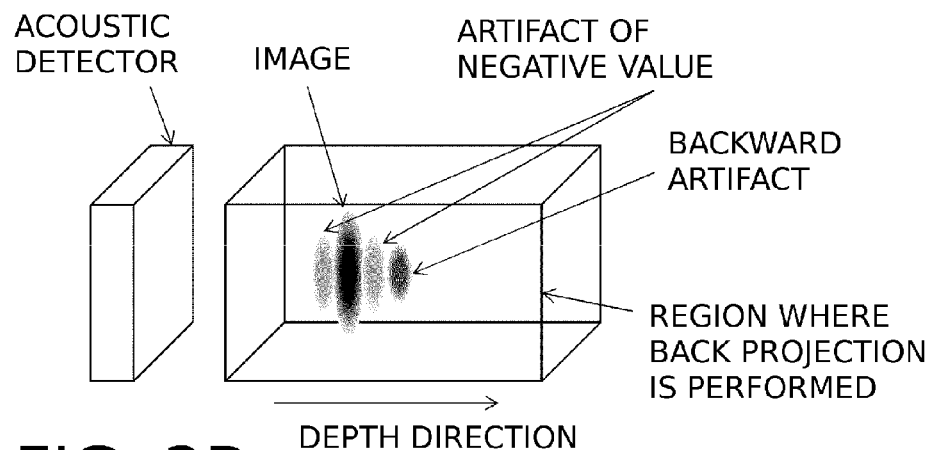

Furthermore, in a situation as shown in FIG. 2B, the real image, and the artifact resulting from the ringing (backward artifact) have the following relation.

A distance between the both is determined by time difference between the signal and the ringing, and is constant in a case of the same acoustic detector.

Additionally, an intensity ratio of the real image and the artifact resulting from the ringing is determined by an intensity ratio of the signal and the ringing. This ringing intensity is changed depending on a frequency component of the signal. A frequency component of the signal resulting from the photoacoustic effect depends on the size of the light absorber, and therefore the intensity ratio of the real image and the artifact resulting from the ringing depends on the size of the light absorber, the intensity ratio thereof is also constant when the size of the light absorber is constant.

A ratio of the size (dimensional ratio) of the real image and the artifact resulting from the ringing is also determined by a wave width of the signal and the ringing. The width of the signal resulting from the photoacoustic effect depends on the size of the light absorber, and therefore the dimensional ratio of the real image and the artifact resulting from the ringing depends on the size of the light absorber, and the dimensional ratio is also constant when the size of the light absorber is constant.

As described above, in a case where a certain image is a real image resulting from the photoacoustic signal generated by difference of the absorption coefficients inside the object, the image is accompanied by an artifact having a certain relation with the real image on the front and back or the back of the real image. On the other hand, in a case where a certain image results from an artifact or noise, no frontward and backward or backward artifact having the aforementioned relation with respect to the image exists. Accordingly, it is determined whether or not the image is a real image, by examining the relation between the image and the frontward and backward artifact or the backward artifact for each acoustic detector. In a case where the artifact resulting from the ringing is present, determination can be made at high accuracy with many conditions as compared with a case where only the artifacts of the negative values located on the front and back of the real image are present. On the basis of such a relation, it is possible to create a template in the similarity distribution generation device described later.

(Processing in Reliability Distribution Generator)

The processing in the reliability distribution generator 7 in Step S5 will be described. Here, the reliability distribution is a distribution indicating difference in intensity by comparing a background signal with other signals (a real image or an artifact) on the basis of the object information distribution. That is, a state where the reliability of object information is high indicates a state where a possibility that a signal in a certain segment of the object is noise of the background is low.

In the present embodiment, the initial sound pressure distribution is taken as the reliability distribution. However, as described later, a distribution of signal-to-noise (S/N) ratios in a part of an image which is targeted, or a distribution of variance values thereof may be used as the reliability distribution.

The initial sound pressure distribution is desirable as the reliability distribution. The initial sound pressure distribution is a distribution obtained by reconstructing an acoustic wave generated from the object and creating image data, and indicates an intensity distribution of the acoustic wave generated inside the object. In the initial sound pressure distribution, a real image derived from an absorber or an artifact, and a background signal are mixed.

In this case, in order to create the reliability distribution, signals in the initial sound pressure distribution need to be separated into the real image and the artifact, and the background (noise). As a separation method, for example, it is conceived that a threshold value is set in the initial sound pressure distribution, and portions having intensity not smaller than the threshold value are left. However, signals of the threshold value or more are not limited to signals derived from the real image, and there is also a possibility that the signals are signals derived from artifacts with high intensity.

As an example of obtaining the reliability distribution, a method using the S/N ratio of the image will be described. In this method, a ratio of the signal intensity to the background in the object information distribution is used.

First, the total values of the object information are converted to such a form as to understand the distribution of the intensity such as a histogram distribution. Then, the background and signals are separated by setting a threshold value from a viewpoint of dysphasic, and a mode value or an average value of the background is obtained. In a case where separation of the background and the signals cannot be performed, an average value of the whole values of the object information distribution is obtained. The S/N ratio of the image is calculated by defining an obtained value of the background as a noise value, and taking a ratio with respect to each voxel value (signal value).

At this time, in a case where the voxel value is smaller than the value of the background, processing of rewriting an S/N ratio in the voxel to a value capable of determining as an error value such as zero, 1, and minus may be performed. The error value may not be given to a voxel with a low value, and an S/N ratio of an image including the voxel may be simply reduced, for example, by 1/10. In this method, the value of the background can be averaged, and therefore the intensity of the signal to the average value can be quantified as the S/N ratio.

As an example of obtaining the reliability distribution, a method using the variance value will be described. In this case, the variance value of the image is defined as a variance value in a partial region of the obtained object information distribution.

A two-dimensional or three-dimensional region is extracted with respect to the object information distribution when the variance value is calculated. Then, the variance value inside the extracted region is obtained. While the variance value is smaller in a real image portion with uniform values in the object information distribution, the variance value tends to become high on a boundary between a non-uniform real image and the background, or a background portion. In this method, the extracted region can be two-dimensionally or three-dimensionally selected, and hence three-dimensional processing is enabled. Additionally, there is an advantage that accuracy of the variance value can be changed by changing the size of the extracted region.

(Processing in Similarity Distribution Generation Device)

The processing in the similarity distribution generation device 6, corresponding to Step S4 will be described. The template data 10 is information indicating the relation between the real image, and the artifacts on the front and back of the real image or the backward artifact. The template data 10 is created from the initial sound pressure distribution in consideration of a response characteristic such as a frequency band characteristic of the acoustic detector.

This information indicating the relation between the real image and the artifact includes at least one of the distance between the real image and the artifact, the intensity of the real image and the artifact, and the size of the real image and the artifact. While the information preferably includes all of the aforementioned distance, intensity, and size, the present invention can be worked as long as at least one of the three is included.

Although the template data 10 is desirably voxel data including the aforementioned relation, may be image data or signal data including the aforementioned relation, a histogram thereof, or the like.

For example, as the template data, a case of using a histogram of intensity is considered. First, a histogram indicating the relation between the real image and the artifact is prepared, and compared with a histogram of three-dimensional voxel data (in this case, calculated initial sound pressure intensity) of a part of the object information distribution.

As another example of the template data, it possible to use one-dimensional voxel data including the relation between a distance and intensity. In this case, it is only necessary to prepare one-dimensional voxel data including a value of intensity corresponding to the relation between the real image and the artifact at a distance between the real image and the artifact, and compare a part of the object information distribution with the one-dimensional voxel data.

Although the initial sound pressure distribution is used as the object information distribution in the present embodiment, an optical property distribution such as an absorption coefficient distribution may be used as in an embodiment described later. Additionally, the response characteristic of the acoustic detector means a characteristic which each acoustic detector peculiarly posses, having a possibility of influencing the relation between the real image and the artifact thereof, and examples thereof include the size of a detection surface and the like in addition to a frequency band characteristic.

In the present invention, a distribution used in matching processing and a distribution used in extraction processing among the object information distribution are referred to as a matching information distribution, and an extraction information distribution, respectively. As described in the after-mentioned respective embodiments, as the matching information distribution and the extraction information distribution, the same kind of object inside information distributions may be used, or other kinds of object inside information distributions may be used. The kinds of the object information distributions used respectively can be appropriately selected according to purposes of measurement.

When the template data is created, it is desirable to simulate measurement of the spherical light absorber after considering the frequency band characteristic of the acoustic detector. However, the light absorber may have a shape other than the spherical shape. Additionally, the template data may be created not by simulation but by actual measurement.

When similarity is determined, data including a certain image obtained by the measurement and an image considered as an artifact thereof is compared with the template data. When the both are similar, it is shown that the relation between the certain image and the image considered as the artifact thereof is close to the relation between a real image and an artifact of the real image. That is, it can be said that there is a high possibility that an image to be determined is the real image and the artifact thereof.

In the matching processor 11, voxel data of the same size as the template data 10 is extracted from a certain position in the initial sound pressure distribution obtained by the object information distribution processor 5, and similarity of the voxel data and the template data 10 is calculated. This initial sound pressure distribution used in this matching processing is the matching information distribution. In a case where the template data 10 is not voxel data, the matching processor generates voxel data or a histogram for matching processing, and calculates the similarity of the histogram or the voxel data extracted from the certain position in the initial sound pressure distribution. Furthermore, the position extracted from the initial sound pressure distribution is moved, and the similarity is calculated. This repeatedly performed to create the similarity distribution.

The similarity distribution is a three-dimensional distribution as a new object information distribution, representing similarity with template data in each of plural voxels in the initial sound pressure distribution. A similarity R is desirably calculated by zero-mean normalized cross-correlation (ZNCC) shown in formula (1). However, a method of calculating a parameter showing similarity, such as sum of squared differences (SSD), and sum of absolute differences (SAD), may be used.

[Math. 1]

$$R = \frac{\sum_{k=0}^{N-1}\sum_{j=0}^{M-1}\sum_{i=0}^{L-1}((I(i,j,k)-\bar{I})(T(i,j,k)-\bar{T}))}{\sqrt{\sum_{k=0}^{N-1}\sum_{j=0}^{M-1}\sum_{i=0}^{L-1}(I(i,j,k)-\bar{I})^2 \times \sum_{k=0}^{N-1}\sum_{j=0}^{M-1}\sum_{i=0}^{L-1}(T(i,j,k)-\bar{T})^2}} \quad (1)$$

where L, M, and N denote the numbers of voxels in directions X, Y, and Z in an XYZ coordinate system respectively, and I(i, j, k) denotes a distribution extracted from the initial sound pressure distribution obtained by the object information distribution processor 5.

$\bar{I}$ [Math. 2]

denotes an average value of the extracted distribution.
T(i, j, k) denotes template data.

$\bar{T}$ [Math. 3]

denotes an average value of the template data.

(Processing in Combination Processor)

The processing in the combination processor 8, which performs the processing of Step S6, will be described. A point of the present invention is to combine the similarity distribution and the reliability distribution.

As described above, the determination of the real image and the artifact can be made by using the similarity distribution. On the other hand, the reliability distribution represents difference (ratio) of the intensity of the background and other signals (the real image and the artifact). The combination processor 8 distinguishes between the background and other signals on the basis of the reliability distribution, and applies the similarity distribution to the remaining real image and artifact, to separate only the real image. Specifically, the real image is clipped to be distinguished from other signals (the artifact, the background) by taking a product of the similarity distribution and the reliability distribution (e.g., initial sound pressure distribution). At this time, a product of a distribution normalized by using a maximum value and the similarity distribution can be taken without directly using the reliability distribution.

<Application Result>

A result of applying the processing of the first embodiment to clinical case data will be shown.

First, a breast (which is in this example the object of examination) is held between holding plates of polymethylpentene, and the acoustic detector is placed through the holding plates. The acoustic detector is a 2D array acoustic detector having a frequency band of 1 MHz±40%. Pulsed light is emitted to the object from a light source A with a wavelength of 797 nm, and the acoustic detector acquires a generated photoacoustic wave to convert the same to signal data. Image reconstruction processing is performed for the acquired signal data by universal back projection, thereby creating an initial sound pressure distribution. A value of the initial sound pressure distribution is voxel data, and 1 voxel is a cube 0.25 mm on each side. The size of the obtained initial sound pressure distribution is 481 voxels long, 185 voxels wide, and 281 voxels tall.

Figure 10A:
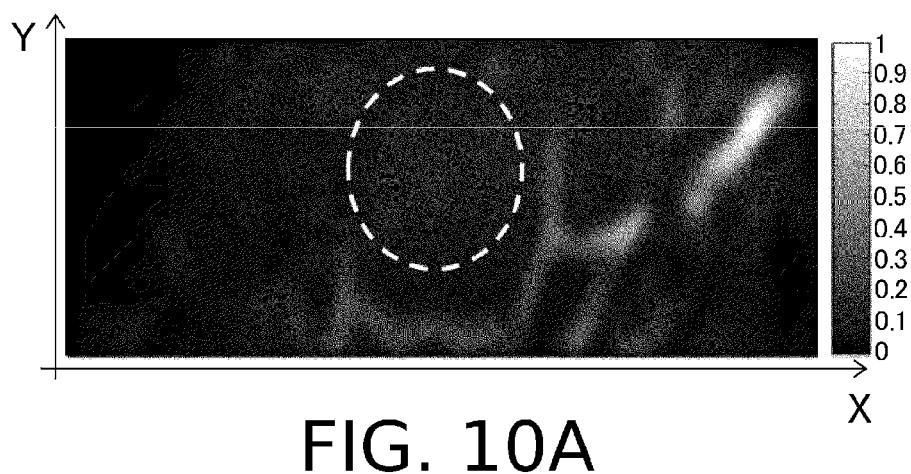
FIGS. 10A and 10B each are a figure showing a situation where the present invention is applied to clinical case data.

FIG. 10A shows a figure in which the initial sound pressure distribution is normalized on a portion of 25 voxels deep in a Z-axis direction by a maximum value.

Figure 10B:
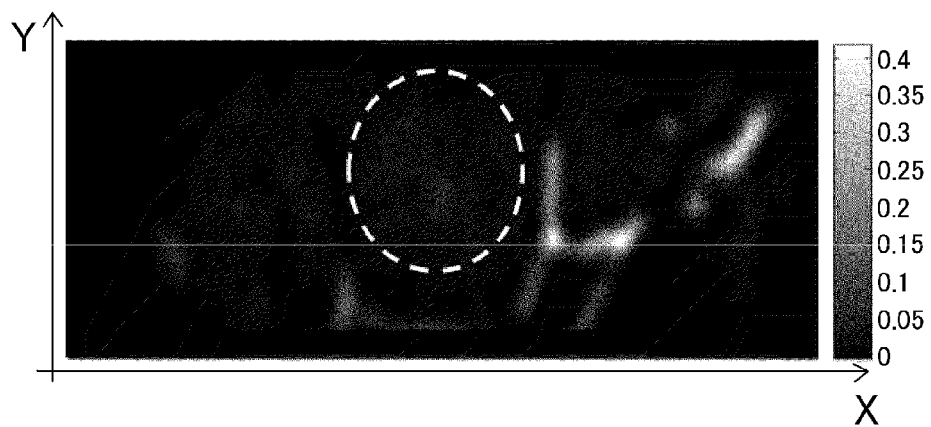

FIG. 10B shows a situation of applying a method of the first embodiment. This figure shows a distribution calculated by calculating a similarity distribution from an initial sound pressure distribution obtained by an image reconstruction processor, and taking a product of the similarity distribution and an initial sound pressure distribution employed as a reliability distribution. Here, normalization is performed by a maximum value of the initial sound pressure distribution. That is, FIG. 10B is a figure at the time of applying this method to the clinical case data.

FIG. 10A and FIG. 10B will be compared. FIG. 10A displays a real image and artifacts which are mixed, and cannot be distinguished. It is found that a background remains in a white broken line portion or the whole of an image. On the other hand, FIG. 10B is a distribution of the product of the similarity distribution and the initial sound pressure distribution, the real image and the artifacts are discriminated, a real image portion remains, and the background can be reduced in the white broken line portion.

Thus, a post-combination processing distribution is displayed, thereby enabling the real image portion to be visually recognized in good contrast.

Second Embodiment

In the present embodiment, an embodiment of performing extraction processing before and after the combination processing of the first embodiment, and displaying an initial sound pressure distribution will be described. A device configuration and an implementation method of the present embodiment are similar to those of the first embodiment except for extraction processing, and therefore different portions will be mainly described.

<Extraction Processing after Combination Processing>

Figure 4:
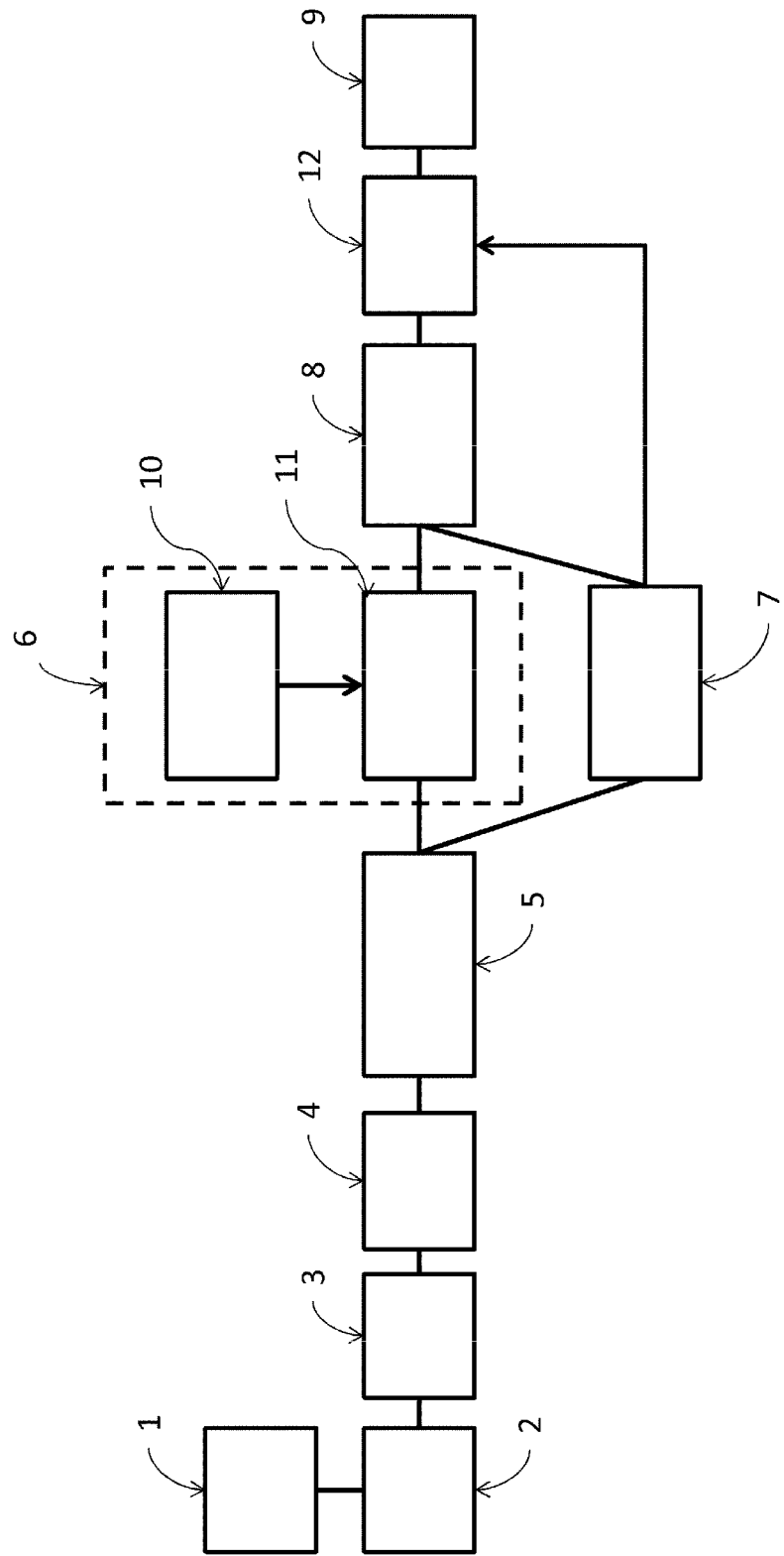
FIG. 4 is an example of a schematic diagram showing a configuration of a device according to a second embodiment.

First, a case of performing extraction processing for a post-combination processing distribution will be described. FIG. 4 shows a configuration of the whole of a device. An extraction processor 12 selects a voxel of a high value in the post-combination processing distribution, and extracts a post-combination processing distribution of the voxels.

Specifically, regions are first extracted from a part or all of the post-combination processing distribution. Then, an arbitrary threshold value is set for each region, and it is determined whether a value after the combination processing of each voxel in the region is higher than the threshold value, or is not higher than the threshold value. At a voxel position of a value higher than the threshold value, the voxel value of the post-combination processing distribution remains with no change, while at a voxel position of a value not higher than the threshold value, the voxel value is rewritten to a value capable of determining as an error value such as zero and minus.

Although such an extraction method is desirable, the error value may not be given to a voxel of a low value, and a sound pressure value of the voxel may be simply reduced, for example, by 1/10.

Additionally, when threshold value processing is performed, processing of normalizing a value of the post-combination processing distribution by using a maximum value may be performed.

Procedure will be described by a flowchart of FIG. 6. Unlikely the flow of FIG. 3, the aforementioned extraction processing is performed for a post-combination processing distribution obtained in Step S6 (Step S8). Finally, the obtained distribution is combined with the initial sound pressure distribution, and displayed (Step S7).

According to the aforementioned procedure, only a portion of an image of the post-combination processing distribution is left, thereby enabling a background portion to be significantly reduced, and enabling a post-combination processing distribution with improved contrast to be calculated. In the extraction processing, processing for leaving the portion of the image is performed, thereby enabling only the portion of the image to be left while keeping quantitativity of a value of the initial sound pressure distribution.

A result obtained when implementing the procedure of the present embodiment for the clinical case data will be shown.

Figure 11:
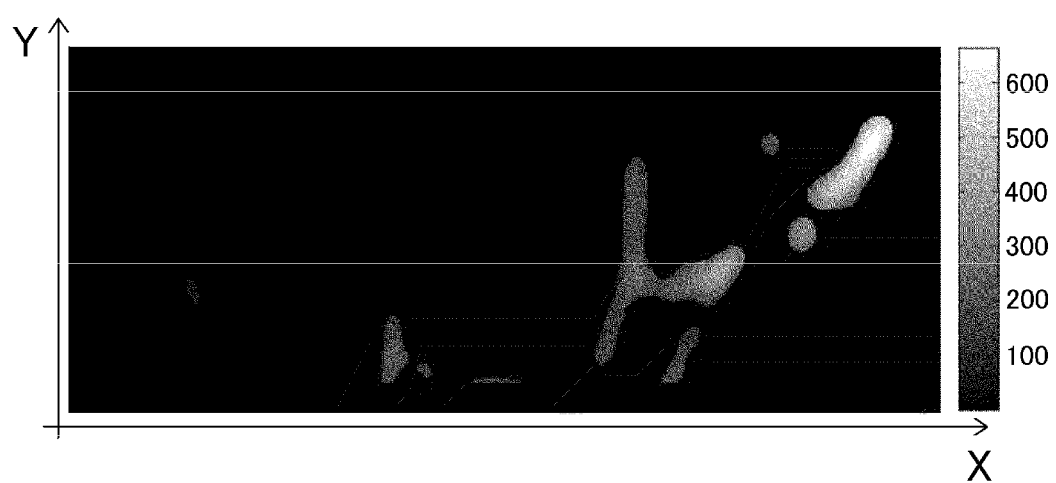
FIG. 11 is another figure showing the situation where the present invention is applied to the clinical case data.

An initial sound pressure distribution obtained by an image reconstruction processor is shown in FIG. 10A, with reference to which the first embodiment is described. A similarity distribution generation device calculated a similarity distribution from the initial sound pressure distribution. On the other hand, a reliability distribution generator generated a normalized initial sound pressure distribution as a reliability distribution. In a combination processor, a post-combination processing distribution was calculated by taking a product of the both. Extraction processing was performed for this post-combination processing distribution while a threshold value is set to 0.05 times maximum intensity, a voxel value higher than the threshold value was extracted, and a voxel value not higher than the threshold value was eliminated. By taking a product of the obtained binarization distribution and the initial sound pressure distribution, a real image portion of the initial sound pressure distribution was extracted and displayed. The situation is shown in FIG. 11. FIG. 11 is a figure at the time of applying this method to the clinical case data. Compared with FIG. 10A, contrast is improved, and an excellent image with a reduced background is obtained in FIG. 11.

By the aforementioned method, an initial sound pressure distribution corresponding to the real image portion with the reduced background portion and improved contrast can be obtained.

<Extraction Processing Before Combination Processing>

Figure 5:
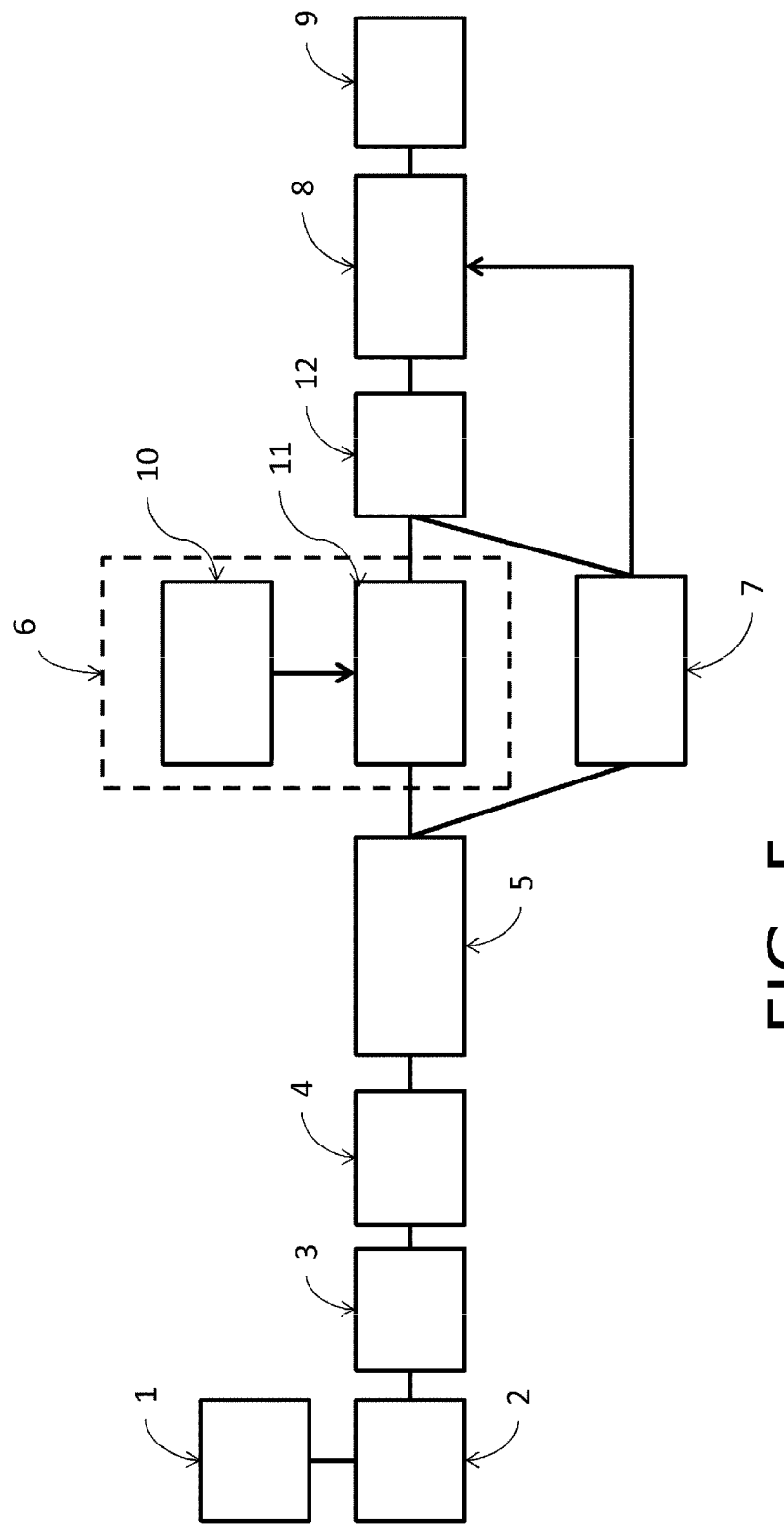
FIG. 5 is another example of the schematic diagram showing the configuration of the device according to the second embodiment.

A case of performing the extraction processing before the combination processor will be described. FIG. 5 shows a configuration of the whole of the device.

The extraction processor 12 of this figure extracts a region of a part or all of a similarity distribution obtained in the similarity distribution generation device, of a reliability distribution, or of the both distributions. An arbitrary threshold value is set for each region. Then, it is determined whether a value of each voxel included in each region is higher than the threshold value, or is not higher than the threshold value. In a case where the value is higher than the threshold value, the voxel value remains with no change, while a value not higher than the threshold value is rewritten to a value capable of determining as an error value such as zero and minus.

Although such an extraction method is desirable, the error value may not be given to a voxel of a low value, and a sound value of the voxel may be simply reduced, for example, by 1/10.

When threshold value processing is performed, processing of normalizing a value of the reliability distribution by using a maximum value may be performed. Furthermore, combination processing may be performed only for a region, for which the extraction processing is performed, may be performed when performing the combination processing.

Figure 6:
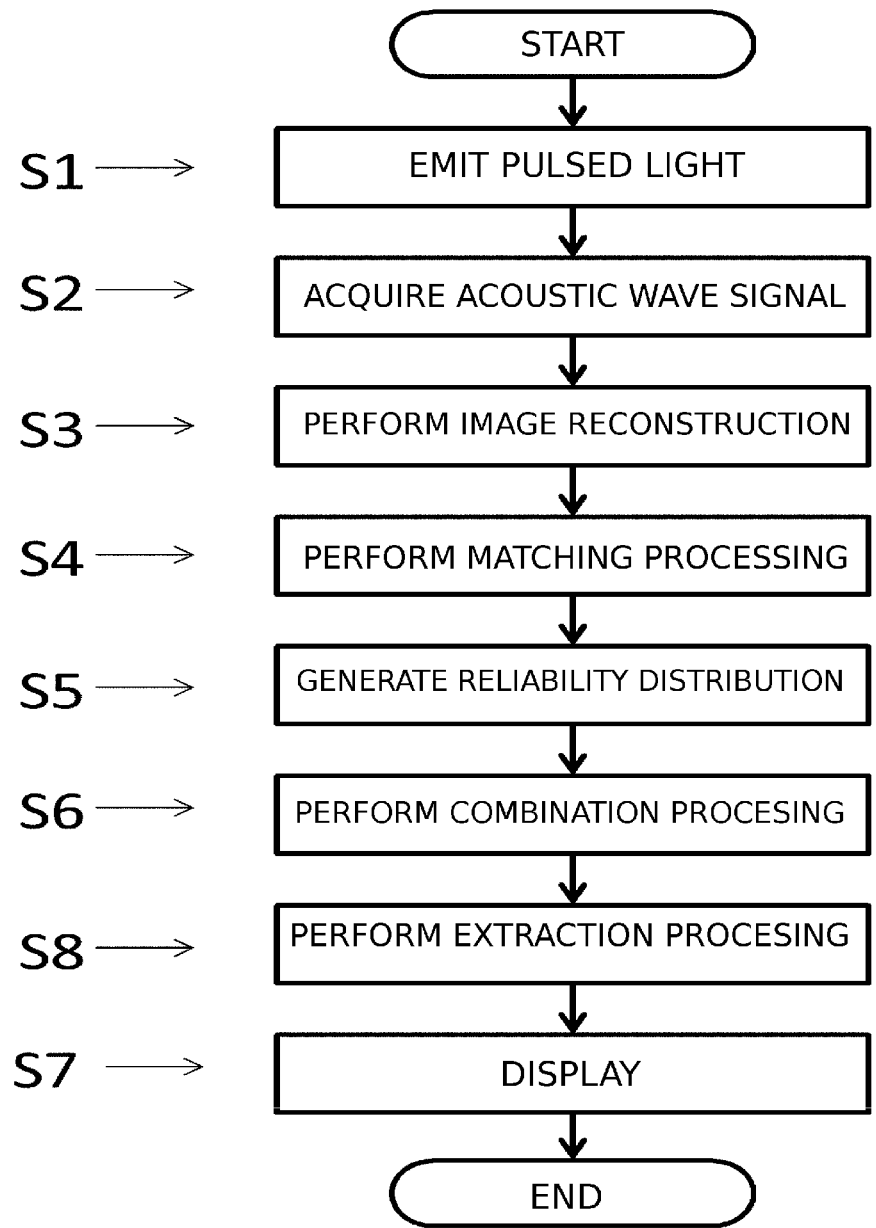
FIG. 6 is a flowchart showing an operation of the device according to the second embodiment.

The procedure for implementing the aforementioned principle is a procedure, in which the order of Step S6 and Step S8 in a flowchart of FIG. 6 is reversed. Finally, the obtained distribution is combined with the initial sound pressure distribution, and displayed (Step S7).

According to the procedure of the present embodiment, only a portion with a value not smaller than the threshold value in the similarity distribution or the reliability distribution is left, thereby enabling a background portion to be significantly reduced, and enabling a post-combination processing distribution with improved contrast to be calculated. Additionally, in a case where the combination processing is performed only for a region, for which the extraction processing is performed, it is expected that a calculation amount is reduced and calculation time is also shortened as compared with a case of calculating the whole regions of the similarity distribution and a reliability distribution. Furthermore, the extraction processing may be performed also for the obtained post-combination processing distribution. A result obtained is similar to that shown in FIG. 11.

Third Embodiment

In the present embodiment, a method for performing display processing for a portion of an image of an absorption coefficient distribution by using a post-combination processing distribution will be described. As to a device configuration and an implementation method, different portions from the aforementioned respective embodiments will be mainly described.

Figure 7:
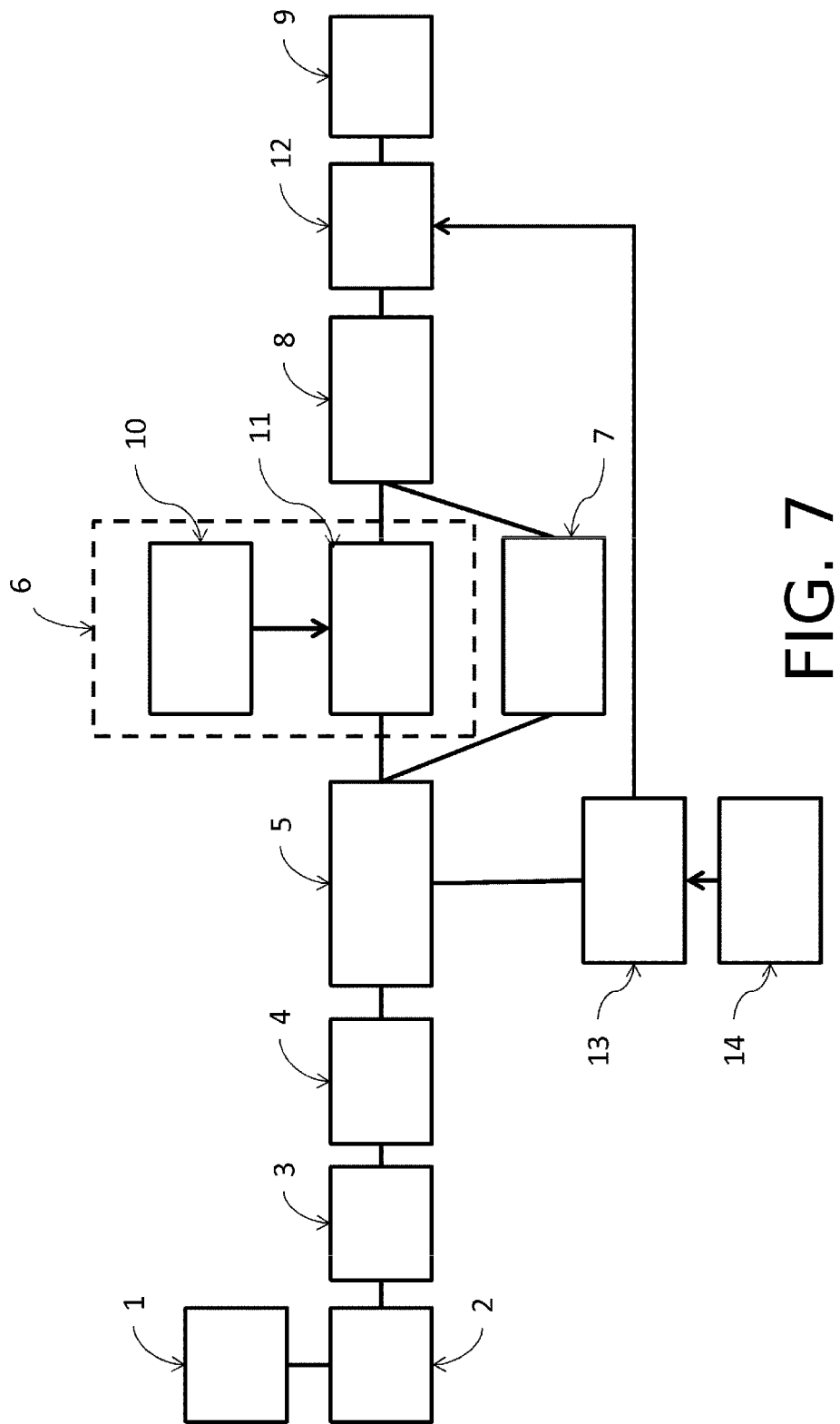
FIG. 7 is a schematic diagram showing a configuration of a device according to a third embodiment.

FIG. 7 shows a device configuration of a third embodiment. Compared with the first half (FIG. 4) of the second embodiment, an absorption coefficient calculator 13 using light volume distribution 14 is added. The absorption coefficient calculator 13 can calculate the absorption coefficient distribution from an initial sound pressure distribution.

Here, initial sound pressure P calculated by an object information distribution processor is expressed by a formula (2).
[Math. 4]

$$P = \Gamma \cdot \mu_a \phi \qquad (2)$$

where $\Gamma$ denotes a Grueneisen constant of a light absorber, $\mu_a$ denotes a absorption coefficient of the light absorber, and $\phi$ denotes light volume of reaching the light absorber. The Grueneisen constant can be considered to be constant, and therefore initial sound pressure is proportional to a product of the absorption coefficient and the light volume. The light volume can be obtained by calculating light propagation inside a biological body from an incident light distribution, and therefore the absorption coefficient can be calculated by dividing the initial sound pressure by the light volume.

The absorption coefficient calculator 13 calculates the absorption coefficient distribution by applying the initial sound pressure distribution obtained from the object information distribution processor 5, and the light volume distribution 14 to the aforementioned formula (2). The light volume distribution 14 should be created by previously measuring and calculating an incident light distribution for each measurement, and stored in a recording medium.

The creation of a similarity distribution in a similarity distribution generation device 6, the generation of a reliability distribution in a reliability distribution generator 7, and the processing of obtaining a product in a combination processor 8 are similar to those of the aforementioned embodiments. In an extraction processor 12, extraction is performed from the absorption coefficient distribution by using the similarity distribution, and a result is displayed on a display unit 9. The obtained result is one obtained by replacing each value of FIG. 11 with the absorption coefficient.

In this embodiment, an image portion of the absorption coefficient distribution can be extracted and displayed by using a post-combination processing distribution. Thus, an absorption coefficient distribution corresponding to a real image portion with a reduced background portion and improved contrast can be obtained.

Fourth Embodiment

In the present embodiment, the present invention is used for concentration of oxygenated hemoglobin in total hemoglobin, namely extraction of oxygen saturation.

Figure 8:
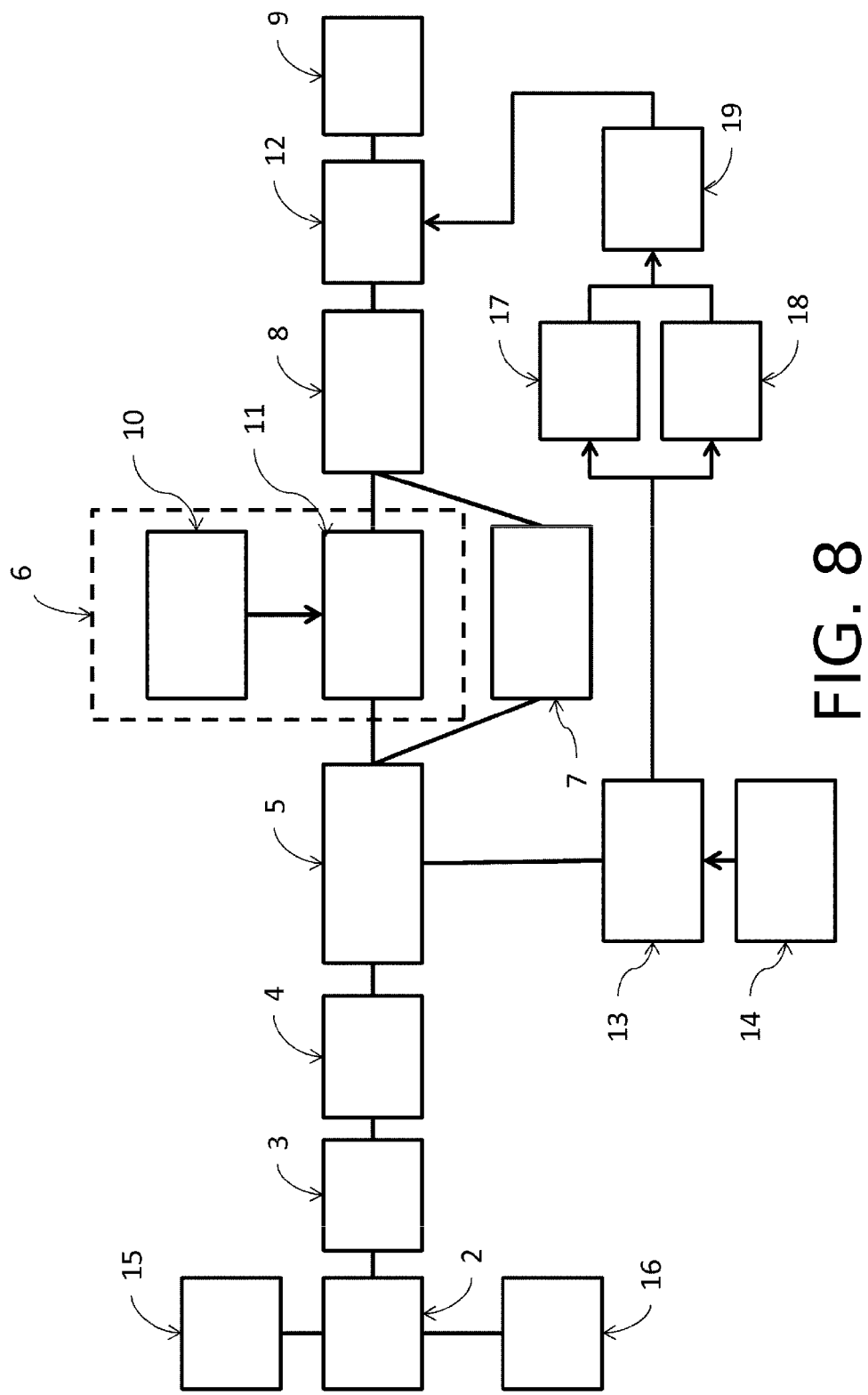
FIG. 8 is a schematic diagram showing a configuration of a device according to a fourth embodiment.

As shown in FIG. 8, in a device configuration, a light source A 15, and a light source B 16 are arranged in placed of the light source 1 of the first embodiment. The light source A and the light source B are different in wavelength, and emit light at different timing. Furthermore, a light source C, a light source D, . . . which are different in wavelength and timing may be added. An oxygen saturation distribution can be calculated by performing comparison processing of absorption coefficient distributions created by the respective light sources. Furthermore, a memory A 17, a memory B 18, and a comparison processor 19 are added as compared with FIG. 7.

An initial sound pressure distribution A created by an object information distribution processor 5 from an acoustic wave resulting from the light source A is converted to an absorption coefficient distribution A by using a light volume distribution 14 previously calculated in an absorption coefficient calculator 13, and stored in the memory A 17. Additionally, as to the light source B, an absorption coefficient distribution B is stored in the memory B 18 similarly. Also in a case where of further including light sources, respective absorption coefficient distributions are stored in a memory C, a memory D, . . . similarly.

Thereafter, in the comparison processor 19, comparison processing (described later) of the absorption coefficient distribution A and the absorption coefficient distribution B is performed, and an oxygen saturation distribution is calculated as a concentration information distribution. In the present embodiment, the comparison processor 19 functions also as a concentration information calculator.

On the other hand, in a matching processor 11, a similarity distribution is created by matching of initial sound pressure distribution created in the object information distribution processor 5 and template data 10. The initial sound pressure distribution used at this time is desirably a distribution created by a light source with a wavelength at which absorption coefficients of oxygenated hemoglobin and reduced hemoglobin are close. At this time, the matching processing may be performed by using only the initial sound pressure distribution formed by one wavelength selected among the wavelengths used in measurement, or the matching processing may be performed for each of a plurality of initial sound pressure distributions obtained by a plurality of wavelengths, and superposition processing may be performed for results. Although a distribution used for matching processing is desirably the initial sound pressure distribution, an absorption coefficient distribution may be used.

In extraction processor 12, extraction processing is performed from the oxygen saturation distribution by using a post-combination processing distribution, and the result is transmitted to the display unit 9.

The oxygen saturation is concentration information which can be calculated by comparing absorption coefficient distributions created by light sources different in wavelength. When a molar absorption coefficient of blood is measured by using light of a wavelength $\lambda_1$ and a wavelength $\lambda_2$, calculated molar absorption coefficients $\mu_a(\lambda_1)$ [mm$^{-1}$], $\mu_a(\lambda_2)$ [mm$^{-1}$] are expressed as in formula (3), and formula (4), where it is assumed that the calculated molar absorption coefficients are low enough to ignore light absorption other than by hemoglobin at wavelength $\lambda_1$ and wavelength $\lambda_2$.
[Math. 5]

$$\mu_a(\lambda_1) = \epsilon_{ox}(\lambda_1) C_{ox} + \epsilon_{de}(\lambda_1) C_{de} \qquad (3)$$

[Math. 6]

$$\mu_a(\lambda_2) = \epsilon_{ox}(\lambda_2) C_{ox} + \epsilon_{de}(\lambda_2) C_{de} \qquad (3)$$

where $C_{ox}$ and $C_{de}$ denote respective amounts (mol) of oxygenated hemoglobin and reduced hemoglobin, and $\epsilon_{ox}(\lambda)$ and $\epsilon_{de}(\lambda)$ each denote respective molar absorption coefficients [mm$^{-1}$ mol$^{-1}$] of oxygenated hemoglobin and reduced hemoglobin at a wavelength $\lambda$.

$\epsilon_{ox}(\lambda)$ and $\epsilon_{de}(\lambda)$ are previously obtained by measurement or literature data, simultaneous equations of the formula (3), and the formula (4) are solved by using measurement values $\mu_a(\lambda_1)$, and $\mu_a(\lambda_2)$, and $C_{ox}$ and $C_{de}$ are obtained. In a case where many light sources are included, the number of formulas is increased by the number of the light sources, and hence $C_{ox}$ and $C_{de}$ are obtained by a least-square method.

The oxygen saturation is defined by a ratio of oxygenated hemoglobin in total hemoglobin as in formula (3), can be calculated as in formula (5), thereby enabling the oxygen saturation to be obtained.

[Math. 7]

$$SO_2 = \frac{C_{ox}}{C_{ox} + C_{de}} \quad (5)$$

In the present embodiment, a problem that an image is not prominent in the oxygen saturation distribution can be solved by performing extraction processing from the oxygen saturation distribution by using the post-combination processing distribution. Although an abundance ratio of hemoglobin is described in the present embodiment, abundance ratios (concentration information distributions) of substances other than hemoglobin can be calculated by a similar principle in photoacoustic tomography, when an absorption spectrum is discriminative. It is also possible to perform extraction processing using the similarity distribution for such concentration information.

A result obtained when the present embodiment is implemented with respect to clinical case data, and a result obtained by using a conventional threshold value method will be shown.

First, a case of cutout of a signal by the conventional threshold value method will be examined.

At this time, a breast which is the object is held between holding plates of polymethylpentene, and acoustic detectors are further placed through polymethylpentene. The acoustic detectors each are a 2D array acoustic detector having a frequency band of 1 MHz±40%. Pulsed light is emitted to the object from the light source A with a wavelength of 756 nm, and the acoustic detector acquires signal data. Then, pulsed light is emitted to the object from the light source B with a wavelength of 797 nm, and the acoustic detector acquires signal data, similarly.

Initial sound pressure distributions of two wavelengths are created by performing image reconstruction of signal data acquired in the respective measurement by using universal back projection. Values of the initial sound pressure distributions each are voxel data, and 1 voxel is a cube 0.25 mm on each side. The size of the obtained each initial sound pressure distribution is 481 voxels long, 185 voxels wide, and 281 voxels tall.

Figure 12A:
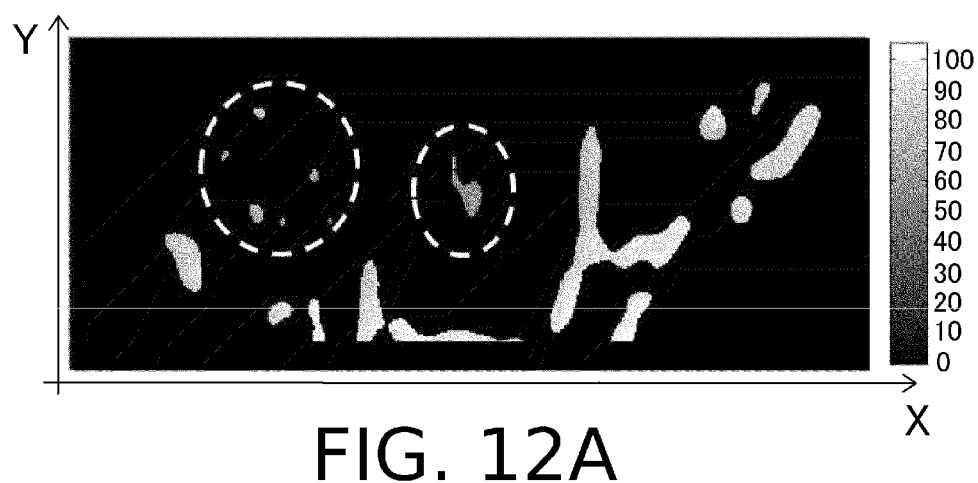
FIGS. 12A and 12B each are yet another figure showing the situation where the present invention is applied to the clinical case data.

The absorption coefficient distributions are calculated by adding already acquired light volume distributions, and the oxygen saturation distribution (%) is calculated by setting threshold values to the absorption coefficient distributions and performing comparison operation. The threshold value is set 0.2 times maximum intensity in each absorption coefficient distribution, and only voxels having intensity higher than the threshold value are displayed in the oxygen saturation distribution. Cutout of signals by this method is the conventional method, and shown in FIG. 12A. FIG. 12A is a figure at the time of applying this method to the clinical case data.

Figure 12B:
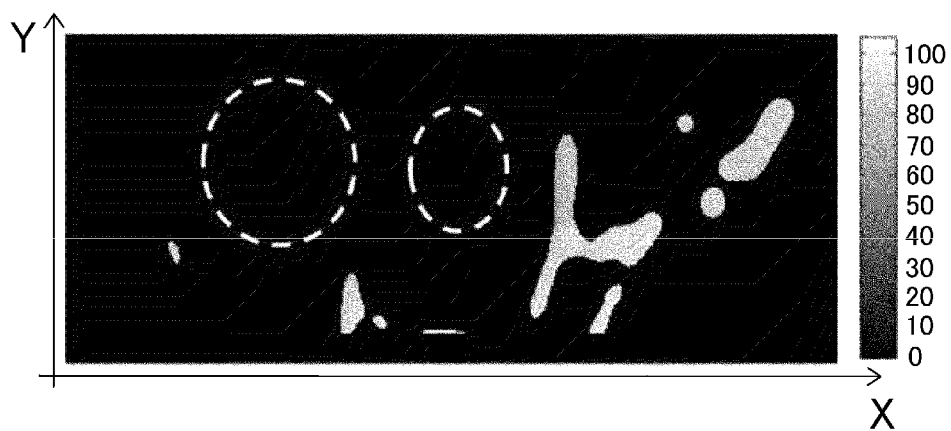

Next, an image obtained in a case of applying a method of the present embodiment is shown. Specifically, an initial sound pressure distribution is first obtained by an image reconstruction processor, a similarity distribution is calculated by a similarity distribution generation device. Then, a product of the similarity distribution, and the initial sound pressure distribution as a reliability distribution is taken in a combination processor. A threshold value is set and binarization is performed for a distribution obtained from this product. Here, the initial sound pressure distribution is normalized by a maximum value, the threshold value is set to 0.05, voxels having intensity higher than 0.05 is set to 1, and voxels having intensity lower than 0.05 is set to zero, for performing binarization. Furthermore, oxygen saturation obtained from the absorption coefficient distributions of two wavelengths is multiplied by a post-combination processing distribution obtained after the aforementioned binarization, thereby enabling cutout of signals. This situation is shown in FIG. 12B. Here, normalization is performed by a maximum value of the post-combination processing distribution. FIG. 12B is a figure at the time of applying this method to the clinical case data.

FIG. 12A and FIG. 12B will be compared. In FIG. 12A, artifacts not derived from absorbers are seen in a white broken line portion. On the other hand, in FIG. 12B, no signal exist at the same place as the white broken line portion of FIG. 12A, and central blood signals are clearly seen. Thus, it can be confirmed that signals derived from the absorbers are cut and separated by using this method, and this method is effective.

Fifth Embodiment

As described in the first embodiment, an intensity ratio of an image and a backward artifact depends on the size of a light absorber. Accordingly, a result of a similarity distribution varies according to the size of the light absorber used when creating template data, and similarity close to the size of the light absorber used when creating the template data is highly valued. In the present embodiment, template data corresponding to the size of each of a plurality of light absorbers is held, and a similarity distribution is created by each template data, and similarity distributions corresponding to the various sizes of the light absorbers are finally created by superimposition.

Figure 9:
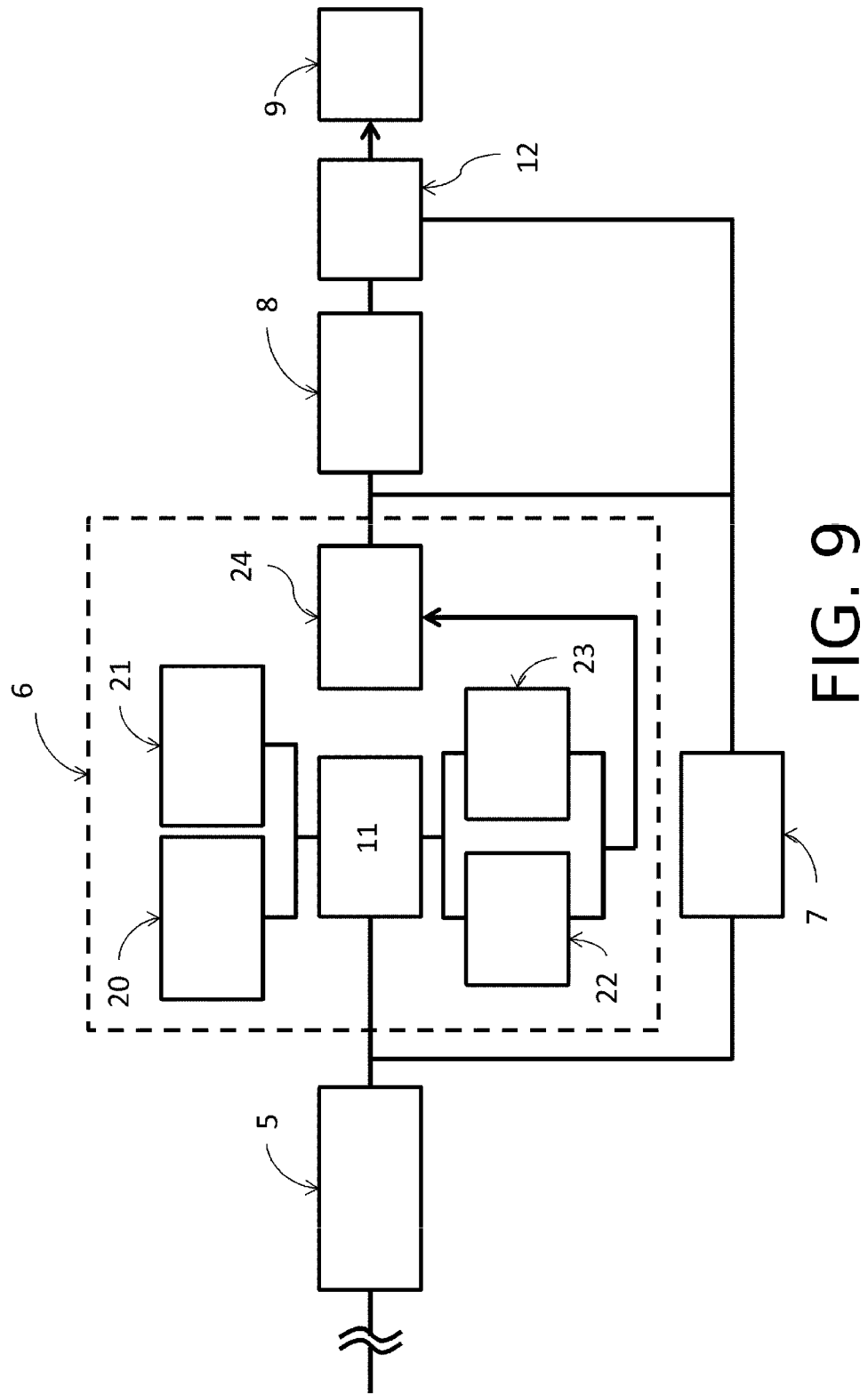
FIG. 9 is a schematic diagram showing an inner configuration of a device according to a fifth embodiment.

A whole device configuration is the same as that of the first embodiment, and an internal configuration of a similarity distribution generation device 6 is different. An internal configuration of the similarity distribution generation device 6 of the present embodiment is shown in FIG. 9. As the template data, template data a (20) and template data b (21) are prepared. The template data a (20) and the template data b (21) are different in the size of the light absorber in simulation at the time of data creation or actual measurement. Although two types of template data are used here, more kinds of template data may be used.

A matching processor 11 performs matching processing of an initial sound pressure distribution from an object information distribution processor 5, and the template data a and the template data b, respectively, create a similarity distribution a, and a similarity distribution b, and stores the respective similarity distributions in a memory a (22) and a memory b (23). A superposition processor 24 superimposes the similarity distribution a and the similarity distribution b to create an integrated similarity distribution. As a superimposition method, although it is desirable to take the average of the similarity distribution a and the similarity distribution b, a method of taking the square root of a product, or a method of taking the root-mean-square may be employed.

Combination processing of obtained integrated similarity distribution and a reliability distribution is performed. Then, in an extraction processor 12, extraction is performed from the initial sound pressure distribution created in the object information distribution processor 5 by using the integrated similarity distribution, and the result is transmitted to an display unit 9. The processing may be performed not only for the initial sound pressure distribution, but also for an absorption coefficient distribution or an oxygen saturation distribution. Additionally, after extraction, an absorption coefficient or oxygen saturation may be obtained and transmitted to the display unit 9.

Figure 13A:
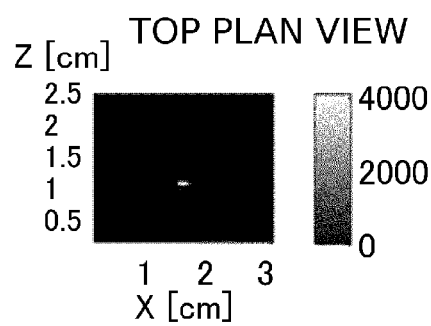
FIGS. 13A to 13C each are a figure showing a situation of imaging according to the fifth embodiment.
Figure 13B:
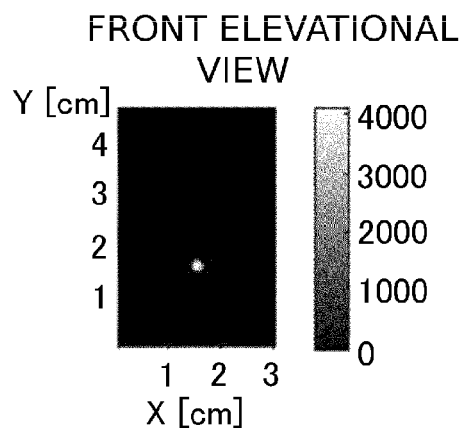
Figure 13C:
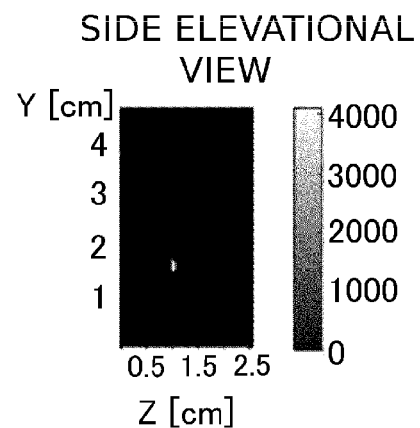
Figure 14A:
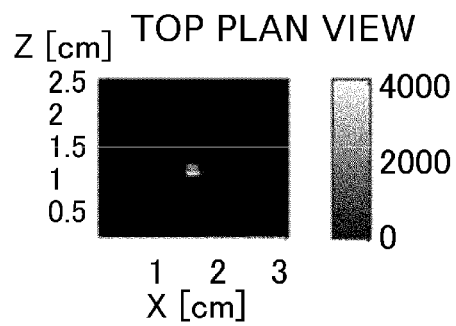
FIGS. 14A to 14C each are a comparative figure showing the situation of the imaging according to the fifth embodiment.
Figure 14B:
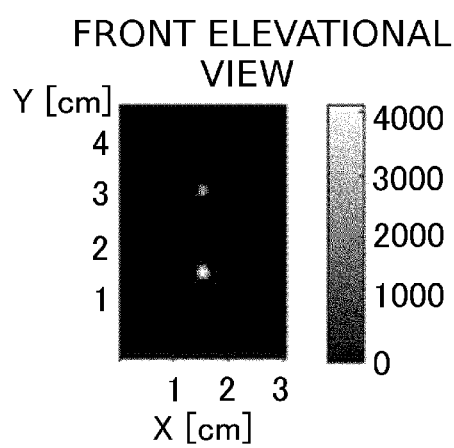
Figure 14C:
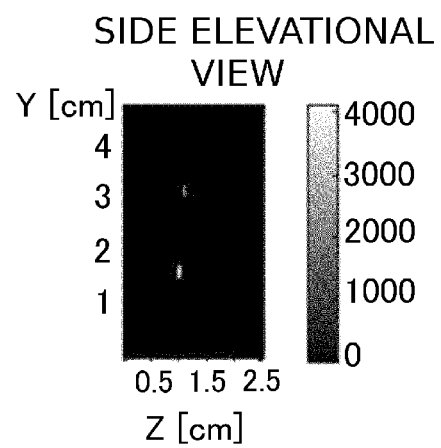

A result obtained when the present embodiment is implemented, and results obtained when only one template data is used as a comparative example are shown in FIG. 13 and FIG. 14. FIG. 13 is an initial sound pressure distribution in a case of using a plurality of pieces of template data. FIG. 13A is a top plan view, FIG. 13B is a front elevational view, and FIG. 13C is a side elevational view. FIG. 14 is an initial sound pressure distribution in a case of using one template data. FIG. 14A is a top plan view, FIG. 14B is a front elevational view, and FIG. 14C is a side elevational view.

A method of simulation will be described below.

An acoustic detector acoustic detector was a 2D array acoustic detector having a frequency band of 1 MHz±40%, and array elements were arranged in a form of 23 array elements in a longitudinal direction×15 array elements in a transverse direction at a width of 2 mm and at a pith of 2 mm. Nanosecond-order pulsed light with a wavelength of 1064 nm was transmitted through water and polymethylpentene to be applied to an object by using a Nd:YAG laser. The object was a simulated biological body having a width of 50 mm, and placed with a light absorber at a distance of 25 mm from the acoustic detector, and an optical property and an acoustic property of a base material conformed to those of fat of a biological body. The sound speed inside the object was set to 1500 m/s, a position of the light absorber was shifted and spheres with diameters of 2 mm and 4 mm are arranged, and oxygenated hemoglobin and reduced hemoglobin were mixed at 4:1. By the simulation, a signal was acquired, reconstruction was performed, and an initial sound pressure distribution as a matching target was obtained.

In order to create template data, as to a light absorber with a diameter of 4 mm, by the simulation, a signal was acquired, reconstruction was performed, and an initial sound pressure distribution simulation was obtained. This initial sound pressure distribution is employed as template data of 4 mm, template matching is performed for an initial sound pressure distribution of the matching target, and a similarity distribution is created. FIG. 13 shows a result obtained by performing extraction from the initial sound pressure distribution of the matching target only on the basis of similarity distribution created by this one template data. A light absorber at a lower portion of the front elevational view is the sphere of 4 mm, and the sphere of 2 mm was not extracted because of low similarity.

Furthermore, in order to create template data, simulation is performed for a light absorber with a diameter of 2 mm, template data of 2 mm was acquired similarly, and a similarity distribution was obtained. An average value of the similarity distribution by the template data of 4 mm and the similarity distribution by the template data of 2 mm was taken, thereby obtaining an integrated similarity distribution. FIG. 14 shows a result obtained by performing extraction from the initial sound pressure distribution of the matching target on the basis of this integrated similarity distribution. As viewing the front elevational view, it is found that the light absorber of 4 mm on the lower portion and the light absorber of 2 mm on the upper portion are displayed.

According to a method of the present embodiment, it has been proved that it is possible to correspond to various sized light absorbers by preparing a plurality of the template data and integrating the respective similarity distributions.

Sixth Embodiment

Each of the aforementioned embodiments targets a device using photoacoustic waves propagating from an object. The present embodiment applies the aforementioned method to an ultrasound device. Although the device configuration is similar to that of the first embodiment, an ultrasound wave is transmitted to the object by using an ultrasound emitting device in place of a light source. A wave received by an acoustic detector is a reflected echo wave. The acoustic detector may double as the ultrasound emitting device.

An object information distribution processor generates an object information distribution on the basis of echo waves. A reliability distribution is generated on the basis of this object information distribution, and is combined with a similarity distribution, thereby creating displayed image data.

Here, in the ultrasound device, initial sound pressure in photoacoustic tomography is not generated, information representing intensity of echo waves, corresponding to difference of acoustic impedance inside the object is acquired. Accordingly, information based on the echo waves is used as the reliability distribution.

As described above, also in the ultrasound device, it is possible to successfully distinguish between a background, and a real image and an artifact by applying the method of the present invention. As a result, display with good contrast can be enabled while reducing artifacts in image data.

In each of the aforementioned embodiments, the present invention is considered as an object information acquiring apparatus using photoacoustic tomography or an ultrasound echo. However, the present invention can be considered also as a control method of controlling the object information acquiring apparatus by using the aforementioned method. Additionally, the present invention can be considered also as a program implementing the control method of the object information acquiring apparatus.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-133801, filed on Jun. 13, 2012, which is hereby incorporated by reference herein in its entirety.

What is claimed is:

1. An object information acquiring apparatus comprising:
   an acoustic detector configured to receive an acoustic wave, the acoustic wave being a photoacoustic wave generated from the object irradiated with light from a light source;
   an object information distribution processor configured to generate an object information distribution representing a property of inside of the object by using a signal derived from the acoustic wave outputted from the acoustic detector;
   a reliability distribution generator configured to generate a reliability distribution by using the object information distribution;
   a similarity distribution generator configured to generate a similarity distribution between template distribution data indicating a relation between a real image and an artifact in the image data, and the object information distribution; and
   a combination processor configured to generate a combined distribution by performing combination processing of the reliability distribution and the similarity distribution.

2. The object information acquiring apparatus according to claim 1, wherein the reliability distribution is information distinguishing between a background noise in the object information distribution, and a component other than the background noise in the object information distribution.

3. The object information acquiring apparatus according to claim 1, wherein the object information distribution is an initial sound pressure distribution of the acoustic wave, an optical energy absorption density distribution inside the object, an absorption coefficient distribution inside the object, or a concentration information distribution of a substance configuring the object.

4. The object information acquiring apparatus according to claim 1, wherein the reliability distribution is an initial sound pressure distribution of the acoustic wave.

5. The object information acquiring apparatus according to claim 1, wherein the reliability distribution is an S/N ratio of the object information distribution.

6. The object information acquiring apparatus according to claim 1, wherein the reliability distribution is a variance value of the object information distribution.

7. The object information acquiring apparatus according to claim 1, wherein the combination processor is configured to perform the combination processing by taking a product of the reliability distribution and the similarity distribution.

8. The object information acquiring apparatus according to claim 1, wherein the combination processor is configured to perform the combination processing by taking a product of a distribution obtained by normalizing the reliability distribution by a maximum value of the reliability distribution, and the similarity distribution.

9. The object information acquiring apparatus according to claim 1, further comprising:
    an extraction processor configured to perform extraction processing of the object information distribution based on comparison of at least one of the similarity distribution and the reliability distribution with a threshold value.

10. The object information acquiring apparatus according to claim 1, further comprising:
    an extraction processor configured to perform extraction processing of the object information distribution based on comparison of the combined distribution obtained by the combination processor with a threshold value.

11. The object information acquiring apparatus according to claim 1, wherein
    the similarity distribution generator is configured to generate a plurality of similarity distributions by calculating similarities between the object information distribution and a plurality of template distribution data, and generate an integrated similarity distribution by integrating the plurality of similarity distributions generated, and
    the combination processor is configured to perform the combination processing of the reliability distribution and the integrated similarity distribution.

12. The object information acquiring apparatus according to claim 1, wherein
    the reliability distribution generator is configured to generate the reliability distribution by using the object information distribution, and
    the template distribution data indicates a relation between a real image and an artifact.

13. The object information acquiring apparatus according to claim 1, wherein the reliability distribution generator is configured to generate the reliability distribution by using the object information distribution.

14. The object information acquiring apparatus according to claim 1, wherein the template distribution data indicates a relation between a real image and an artifact.

15. The object information acquiring apparatus according to claim 3, wherein the concentration information distribution is an oxygen saturation distribution, an oxygenated hemoglobin concentration distribution, or a deoxygenated hemoglobin concentration distribution.

16. The object information acquiring apparatus according to claim 1, wherein the combination processor is configured to generate a combined object information distribution by combining the combined distribution with the object information distribution.

17. The object information acquiring apparatus according to claim 1, wherein
    the object information distribution processor is configured to generate an oxygen saturation distribution as the object information distribution,
    the reliability distribution generator is configured to generate the reliability distribution by using a statistic information of the object information distribution, and
    the combination processor is configured to generate a combined oxygen saturation distribution by combining the combined distribution with the oxygen saturation distribution.

18. The object information acquiring apparatus according to claim 17, wherein the statistic information distribution is a mode value, an average value, or a variance value.

19. The object information acquiring apparatus according to claim 1, wherein the combination processor is configured to cause a display to display the combined distribution.

20. The object information acquiring apparatus according to claim 16, wherein the combination processor is configured to cause a display to display the combined object information distribution.

21. An object information acquiring method comprising the steps of:
    generating an object information distribution representing a property of an object by using a signal outputted from an acoustic detector by reception of an acoustic wave with the acoustic detector, the acoustic wave being a photoacoustic wave generated from the object irradiated with light;
    generating a reliability distribution by using the object information distribution;
    generating a similarity distribution between template distribution data indicating a relation between a real image and an artifact in the image data, and the object information distribution; and
    performing combination processing of the reliability distribution and the similarity distribution.

22. The object information acquiring method according to claim 21, wherein
    the reliability distribution is generated by using the object information distribution, and
    the template distribution data indicates a relation between a real image and an artifact.

* * * * *